US006513803B2

(12) United States Patent
Morales et al.

(10) Patent No.: US 6,513,803 B2
(45) Date of Patent: Feb. 4, 2003

(54) PATHOLOGY GROSSING BOARD

(75) Inventors: Azorides R. Morales, Miami, FL (US); Ervin Essenfeld, Caracas (VE); Harold Essenfeld, Caracas (VE)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 09/876,167

(22) Filed: Jun. 8, 2001

(65) Prior Publication Data

US 2002/0020276 A1 Feb. 21, 2002

Related U.S. Application Data

(60) Provisional application No. 60/210,452, filed on Jun. 9, 2000.

(51) Int. Cl.[7] .................................................. B23Q 3/00
(52) U.S. Cl. ............. 269/290; 269/302.01; 269/289 R; 269/15
(58) Field of Search ........................ 269/289 R, 302.01, 269/15, 13, 901, 909, 290

(56) References Cited

U.S. PATENT DOCUMENTS

| 3,298,411 A | | 1/1967 | Rosett | |
|---|---|---|---|---|
| 3,361,019 A | | 1/1968 | Weiskopf | |
| 3,598,164 A | * | 8/1971 | August | 146/215 |
| 3,799,029 A | | 3/1974 | Cole et al. | |
| 3,987,541 A | * | 10/1976 | Sieczkiewicz | 30/114 |
| 3,995,844 A | * | 12/1976 | Hellman | 269/54.5 |
| 4,094,221 A | * | 6/1978 | Jacoby | 83/762 |
| 4,189,132 A | * | 2/1980 | Di Russo | 269/295 |
| 4,754,675 A | | 7/1988 | Segal | |
| 4,756,519 A | * | 7/1988 | Lilja | 269/302.1 |
| 5,082,254 A | | 1/1992 | Hunnell et al. | |
| 5,527,208 A | * | 6/1996 | Blake | 451/367 |
| 5,664,474 A | * | 9/1997 | Punt | 83/761 |
| 5,817,032 A | * | 10/1998 | Williamson | 600/562 |
| 5,817,103 A | * | 10/1998 | Bell | 606/120 |
| 6,207,408 B1 | | 3/2001 | Essenfeld et al. | |
| 6,359,239 B1 | * | 3/2002 | Missler | 177/25.16 |
| 6,371,470 B1 | * | 4/2002 | Ward | 269/289 R |

FOREIGN PATENT DOCUMENTS

| WO | WO 99/09390 | 2/1999 |
|---|---|---|
| WO | WO 01/44783 A1 | 6/2001 |
| WO | WO 01/44784 A1 | 6/2001 |

* cited by examiner

*Primary Examiner*—Joseph J. Hail, III
*Assistant Examiner*—Daniel Shanley
(74) *Attorney, Agent, or Firm*—Nixon & Vanderhye P.C.

(57) ABSTRACT

A grossing board for preparing gross tissue samples having relatively uniform thickness features one or more tissue-receiving depressions and one or more knife-guiding members. The bottom surface of a tissue-receiving depression is essentially parallel to the upper, cutting surface of the grossing board, and the knife-guiding members are configured to guide the pathologist's knife so as to ensure cuts that are parallel to the bottom surface of the tissue-receiving depression, thereby yielding gross tissue samples of desired reproducible, uniform thickness.

20 Claims, 12 Drawing Sheets

PATHOLOGY GROSSING BOARD

This application claims the benefit of U.S. Provisional Application No. 60/210,452, filed Jun. 9, 2000.

FIELD OF THE INVENTION

The invention relates to instruments used to prepare tissue samples and, in particular, to a grossing board for preparing slices of tissue uniformly of the desired thickness.

BACKGROUND OF THE INVENTION

In the field of pathology, it is customary to prepare slice-shaped tissue samples for processing, microtomy, staining and histopathologic analysis. The term "grossing" refers to the handling and preparation of relatively thick tissue samples, i.e., samples on the order of 0.5 to 4 millimeters thick. This is in contrast to microtomy, in which extremely thin (i.e., on the order of 3 to 10 microns thick) tissue samples are prepared.

When preparing the relatively thick slices from various tissue samples, i.e., when grossing multiple specimens, it is important for the slices of tissue to be as consistently uniform in thickness as possible to facilitate standardization of the tissue processing method.

SUMMARY OF THE INVENTION

The present invention provides a grossing board which facilitates the preparation of gross tissue samples that are of desired thickness. To that end, the invention provides a grossing board having one or more tissue-receiving depressions formed therein. The depressions extend below the upper, cutting surface of the grossing board, and the bottom surfaces of the depressions are parallel to the cutting surface. A knife-guiding assembly is provided to guide the knife or scalpel blade along the surface of the grossing board as the pathologist cuts the tissue sample, thereby yielding gross tissue samples that have essentially uniform thickness.

In preferred embodiments, the knife-guiding assembly features a slotted metal plate that is fastened to one edge of the grossing board, with the slot or slots therein positioned to extend along the edge of the upper, cutting surface of the grossing board, and a metal rod or bar that is positioned inwardly (i.e., toward the central portion of the grossing board) with respect to the slotted metal plate. The metal bar or rod is positioned slightly above the cutting surface of the grossing board to permit the blade of the pathologist's knife to fit under it. Preferably, the tissue-receiving depressions are located between the slotted metal plate and the metal rod or bar, and the metal rod or bar extends parallel to the edge of the grossing board to which the slotted metal plate is attached and hence parallel to the slotted metal plate.

In preferred embodiments, a plurality of tissue-receiving depressions are provided. The various tissue-receiving depressions may each have a different depth so as to produce tissue samples with different thicknesses and/or a different cross-sectional area so as to accommodate tissue specimens of varying proportions.

BRIEF DESCRIPTION OF THE DRAWINGS

The invention will now be described in greater detail in connection with the drawings, in which.

DETAILED DESCRIPTION OF PREFERRED EMBODIMENTS

As shown in FIGS. 1–4, a grossing board 10 according to the invention is assembled from a relatively flat cutting board 12 having an essentially flat cutting surface 14, a lower surface 15 (see FIG. 5) essentially parallel to the cutting surface 14, and side surfaces 18, 20, 22 and 24. The cutting board preferably is made from adhesion-resistant, stain-resistant material such as polypropylene, TEFLON polytetrafluoroethylene, or other plastic material. Any appropriate material may be used for the cutting board.

A number of tissue-receiving depressions 26, e.g. three, are provided in the cutting board. Each of the tissue-receiving depressions is formed such that the lower surface 28 thereof is essentially parallel to the cutting surface 14, thereby providing each of the tissue-receiving depressions with an essentially uniform depth. Preferably, the lower surfaces 28 are textured, e.g. by securing a flat piece of perforated, dimpled metal (like that used in a food grater) to each of them, so as to prevent the mass of tissue placed therein for grossing (as described below) from sliding around, which would make grossing of the tissue more difficult. Preferably, the tissue-receiving depressions vary in depth, e.g. from 0.5 millimeters to on the order of 4.0 millimeters, preferably by even increments or gradations, with the total number of tissue-receiving depressions provided being dependent on the range of tissue sample thicknesses and fineness of the thickness increments desired. The tissue-receiving depressions also preferably vary in cross-sectional area, from on the order of twenty-five millimeters by fifteen millimeters to on the order of thirty millimeters by twenty-five millimeters, to accommodate bulk tissue samples of varying proportions. Alternatively, smaller or larger depressions may be used.

As further illustrated in FIGS. 1–4, the tissue-receiving depressions preferably are formed generally next to one of the side surfaces, e.g. side surface 18, which side of the grossing board may be referred to as the working side. A knife-guiding assembly 30 is secured to the cutting board near the working side. In particular, a flat metal (preferably stainless steel) bearing plate 32 is secured to the cutting surface of the cutting board by means of fasteners 34 such as screws. The bearing plate provides a surface against which the grossing knife or scalpel bears when the tissue sample is being grossed. Preferably, the upper surface of the bearing plate is flush with the cutting surface 14 of the cutting board, which is accomplished by providing a cut-out 35 into which the bearing plate 32 fits. The tissue-receiving depressions 26 are formed by cut-outs 36, which are formed as generally square or rectangular apertures extending at least partly through the bearing plate 32 and which are generally congruent with the tissue-receiving depressions 26 formed in the cutting board.

Figure 5:
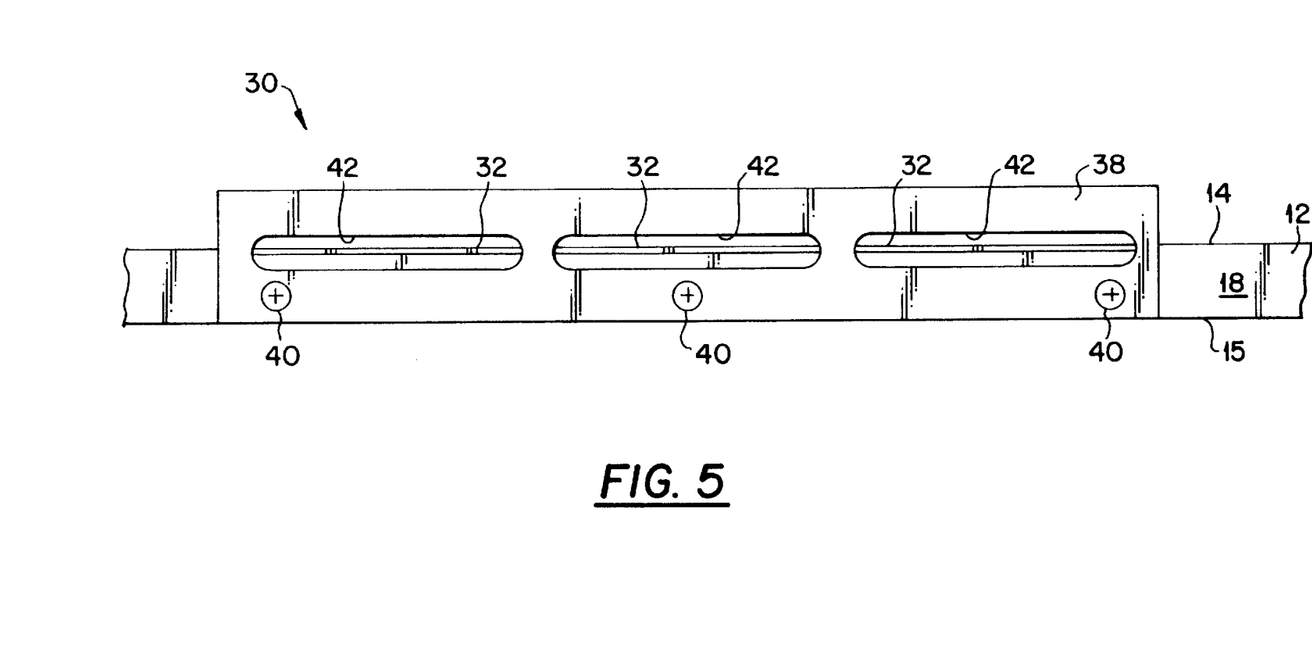
FIG. 5 is an end view of the working side of the grossing board shown in FIGS. 1–4.

A first knife-guiding member 38 is attached to the side surface at the working side of the grossing board by means of fasteners 40, e.g., screws. In one embodiment, the first knife-guiding member 38 is formed from a flat plate of stainless steel with a series of slits 42 (or, alternatively, a single continuous slit) formed therein, which slits are positioned generally at the level of the cutting surface 14 of the cutting board 12 as shown in FIG. 5. The slits 42 are preferably only slightly wider than the thickness of the scalpel or grossing knife typically used for preparing a gross specimen.

A second knife-guiding member 44 is bolted to the grossing board spaced apart from and preferably extending parallel to the first knifeguiding member. In particular, the second knife-guiding member preferably is a stainless steel bar or rod which is secured to the grossing board slightly above the grossing board, i.e., such that a knife blade-receiving gap is formed between the top surface of the bearing plate 32 and the bottom of the metal bar or rod. This may be effected by means of shims or spacers (such as washers provided around the securing bolts) disposed between the bearing plate and the bar or the rod.

Alternatively, in another embodiment, the first knife-guiding member could be provided by means of a rod or bar configured like the second knife-guiding member, i.e., positioned slightly above the upper surface of the bearing plate so as to form a knife-receiving gap thereunder. Furthermore, it is also contemplated that the invention could be practiced with just a single knife-guiding member, whether affixed on or near the working side of the cutting board, like the first knife-guiding member described above, or inwardly, like the second knife-guiding member.

A removable insert 48 is provided and fits within cut-out 50 that is formed in the cutting surface of the grossing board, e.g., by milling. An additional insert 48' and cut-out 50' may also be provided, as illustrated in the embodiment shown in FIG. 6, addressed in greater detail below. That additional insert 48' is located off-center relative to the cutting board 12, between the insert 48 and the side surface 20. Other locations of the inserts 48 and 48', as well as further additional inserts, are contemplated. The inserts may be made of cork, rubber, dental paraffin wax, or other appropriate material which is softer than the material of the cutting board. The upper surfaces of the inserts preferably are flush with the cutting surface of the cutting board. The inserts provide a convenient surface on which to pare the bulk specimen down to smaller portions and, because the inserts are made of material that is considerably softer than the plastic of the cutting board, the pathologist's knife will not become dull from cutting into the inserts nearly as quickly as it would from cutting into the plastic cutting board.

Figure 1:
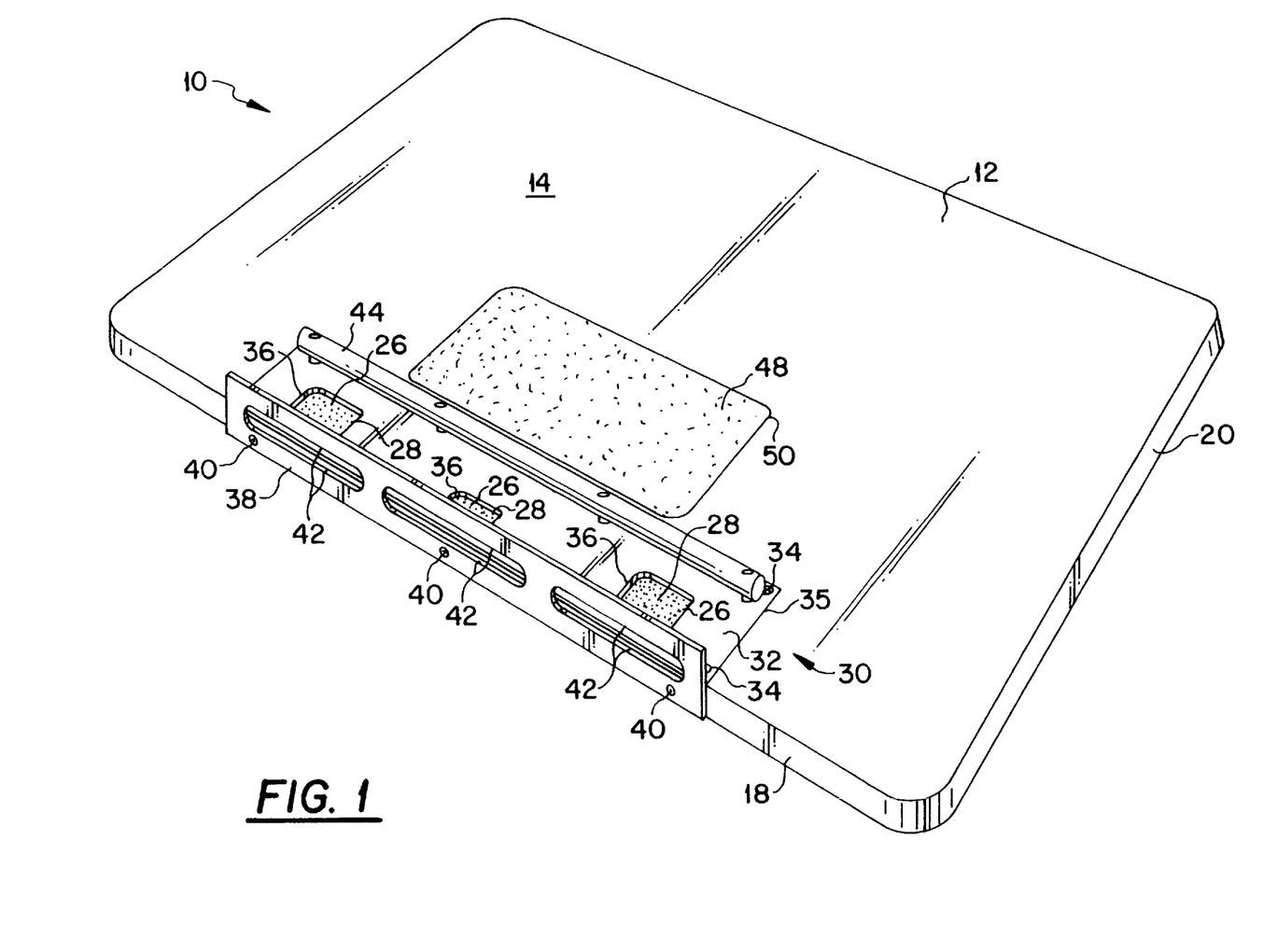
FIGS. 1–4 are perspective views of one embodiment of a grossing board according to the invention, with FIGS. 2–4 illustrating the use thereof.
Figure 2:
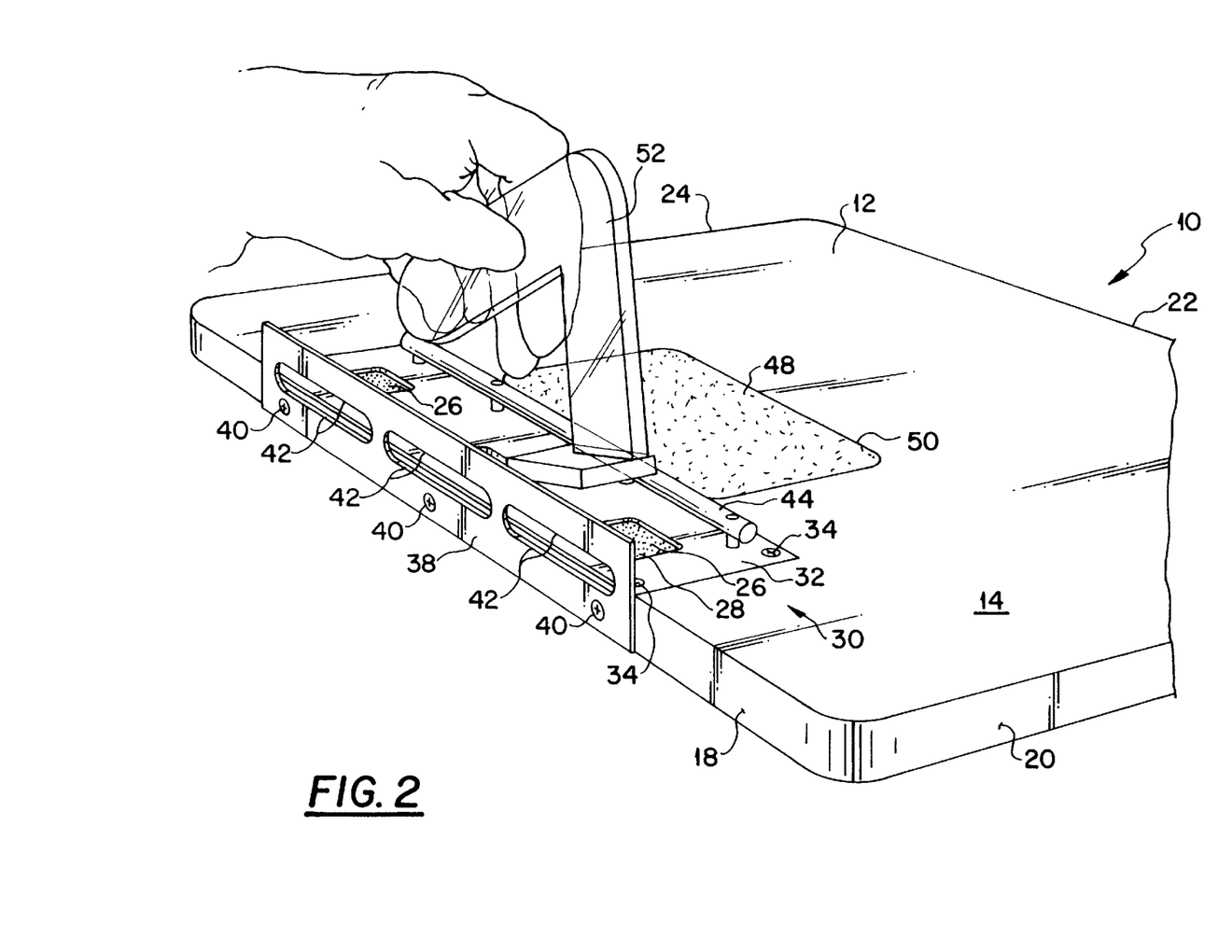
Figure 3:
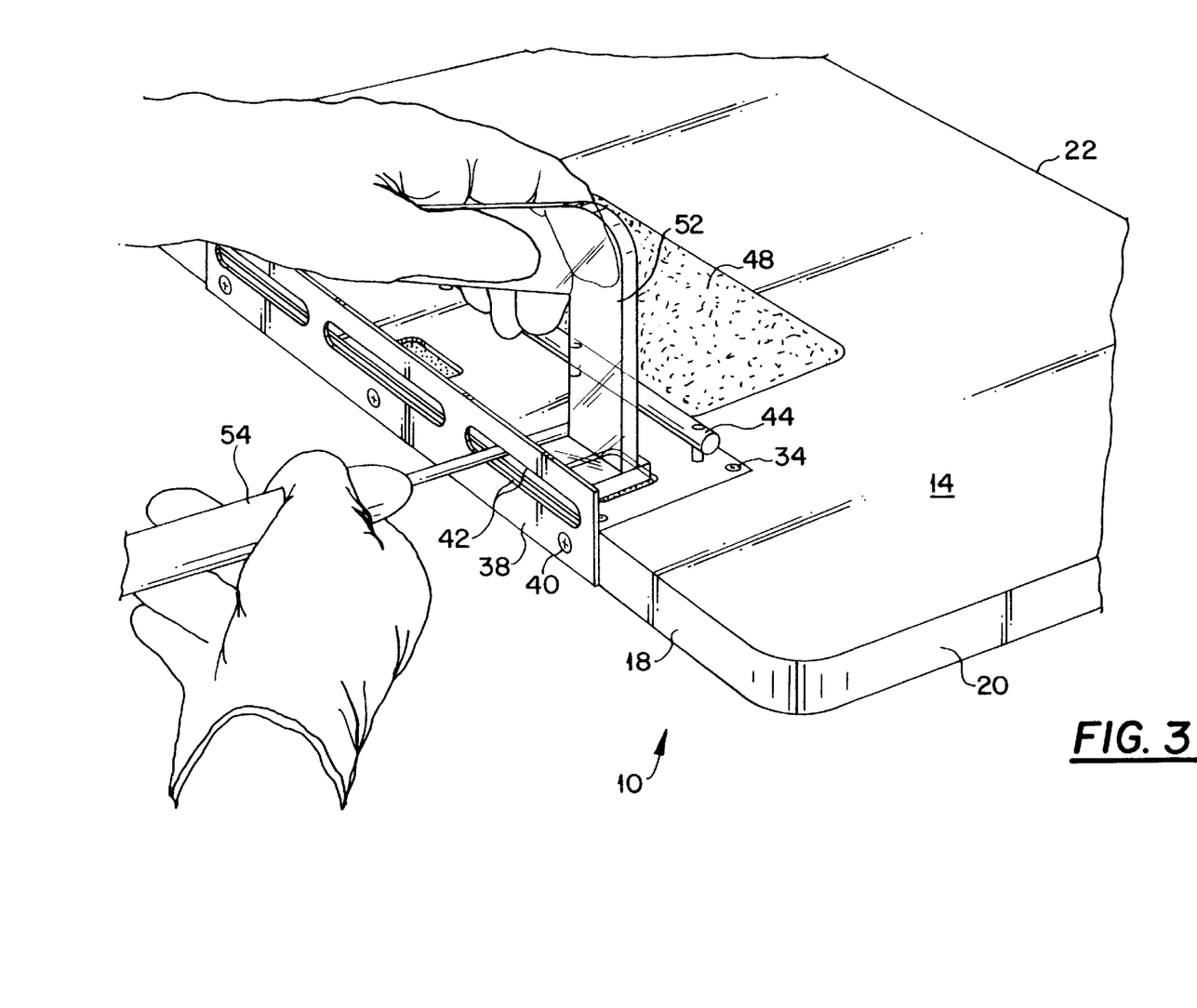
Figure 4:
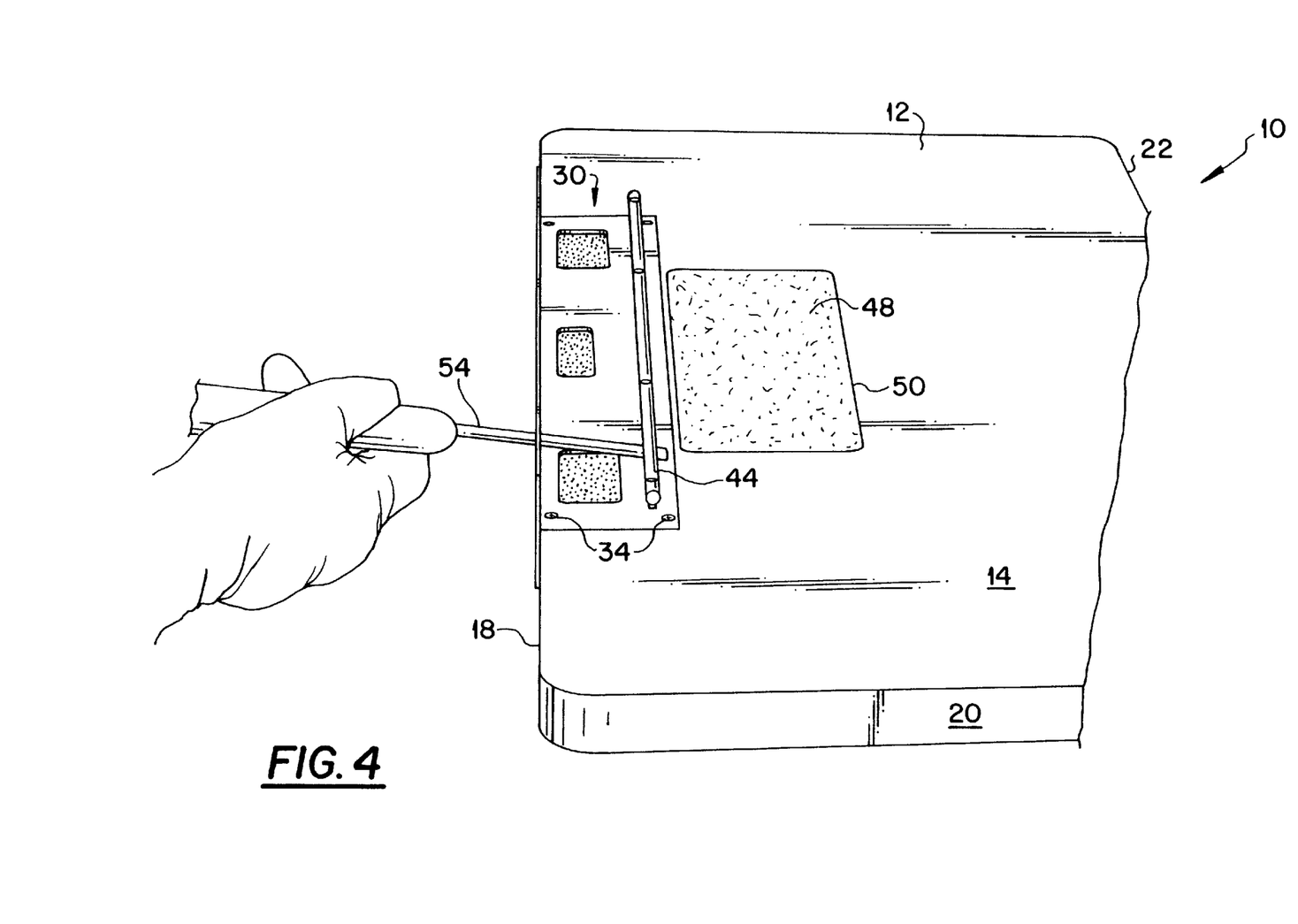

Use of a grossing board according to the invention is illustrated in FIGS. 2–4. In particular, once the pathologist has cut the mass tissue sample down to smaller proportions, e.g., on the order of 1.0 cm×1.0 cm×0.5 cm, he or she places the smaller portion of tissue sample into a selected tissue-receiving depression and holds it securely therein, preferably using a clear acrylic tissue clamp 52 (clear so as to permit viewing of the sample beneath it), as illustrated in FIGS. 2 and 3. The pathologist inserts the blade of his or her grossing knife 54 through the appropriate slit or portion of a slit 42 in the first knife-guiding member 38 and through the gap formed between the bottom of the second knife-guiding member and the top of the bearing plate 32, then cuts across the tissue sample as shown in FIG. 3 by drawing the knife back and forth across the sample underneath the "foot" portion of the tissue clamp 52 to make a smooth, flat cut. This yields a relatively flat surface that is parallel to the bottom surface of the tissue sample that is being held against the lower surface 28 of the tissue-receiving depression. The procedure thus provides a gross tissue sample having a uniform desired thickness.

If the pathologist is particularly skillful, he or she may perform this procedure without the benefit of the tissue clamp, as shown in FIG. 4 or by simply holding the tissue in place using, for example, his or her index finger. This might be done when the tissue sample being grossed is already relatively thin, such that the grossing operation does little more than "shave" the upper surface off of the tissue sample and such that there is essentially little, if any, tissue against which the tissue clamp could bear.

Figure 6:
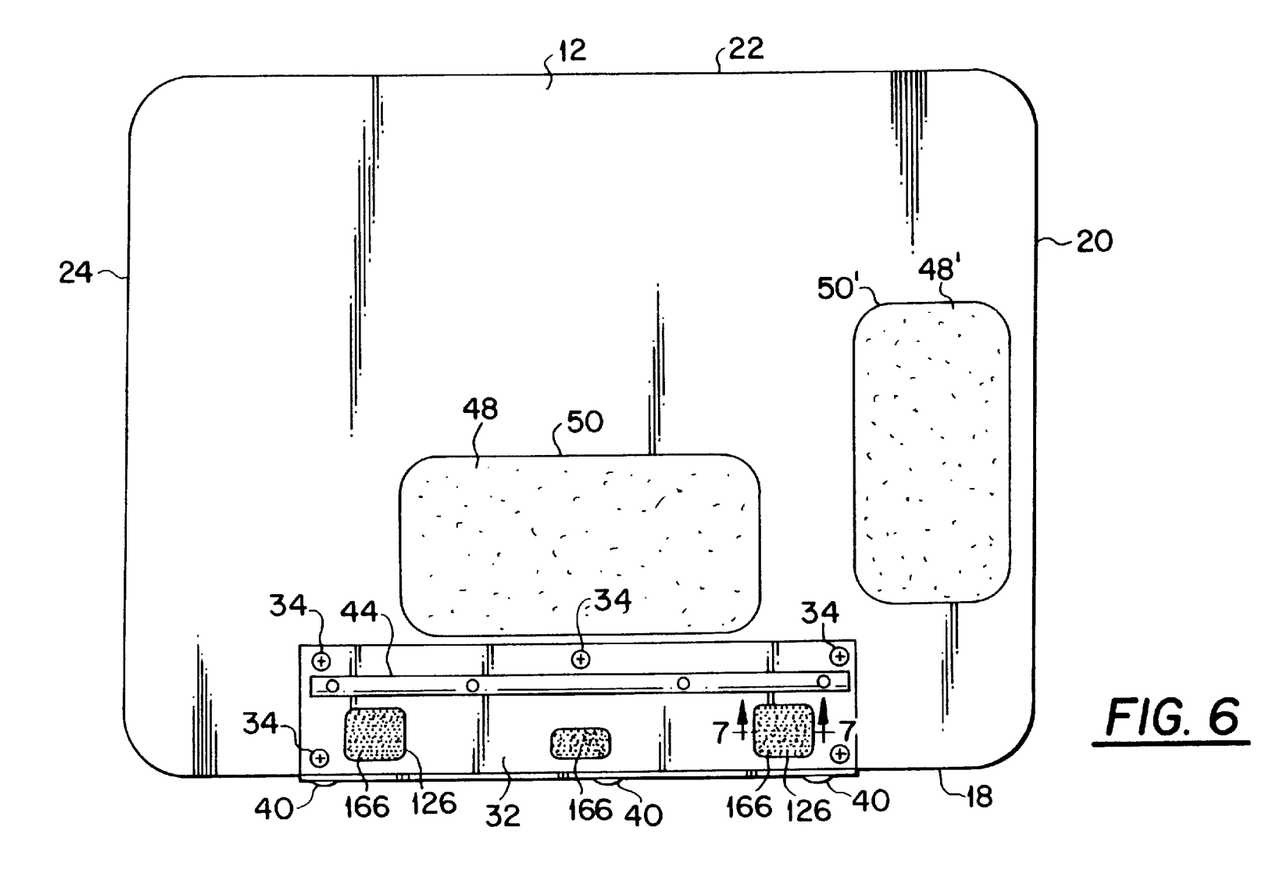
FIG. 6 is a plan view of another embodiment of a grossing board according to the invention.
Figure 7:
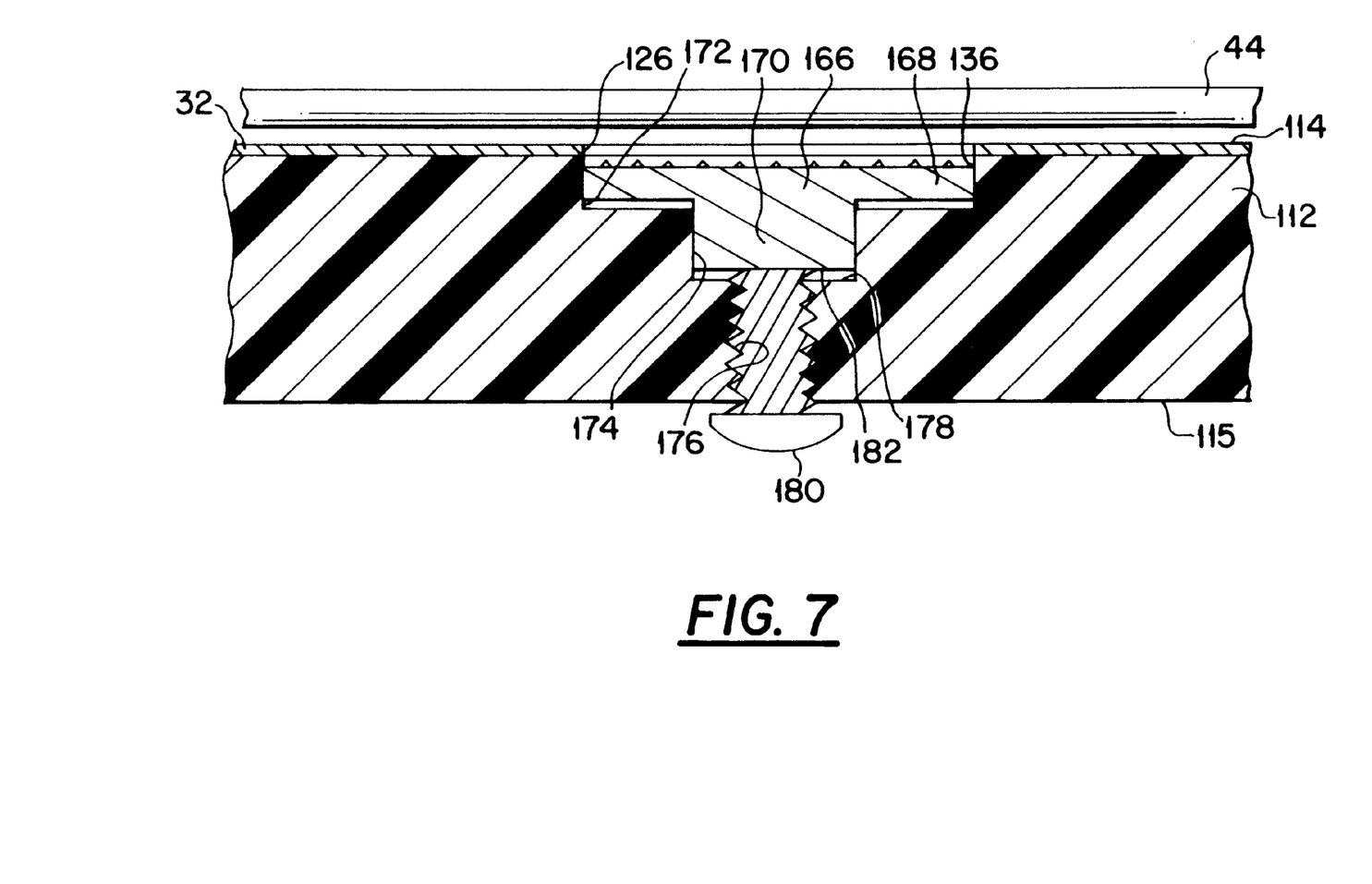
FIG. 7 is a section view taken along line 7—7 in FIG. 6.

According to another embodiment of the invention, illustrated in FIGS. 6 and 7, the depth of each of the tissue-receiving depressions 126 may be adjustable. In particular, as illustrated in FIG. 7, the grossing board may be provided with insert members 166 adjustably positioned within cut-outs 136. As shown in FIG. 7, each insert member 166 includes a support platform portion 168 and a circular post portion 170 extending from the bottom of the support platform portion 168. The cut-outs 136 have a stepped configuration, with a first rectangular recess 172 within which the platform portion 168 fits and a blind, circular bore portion 174 into which the post portion 170 fits. A threaded opening 176 extends between the lower surface 115 of the cutting board 112 and a bottom surface 178 of the blind bore 174. A threaded member 180 (e.g., a bolt) is screwed into the threaded opening 176 to abut and support the bottom surface 182 of the insert member 166. In this manner, the vertical position of the insert member 166 relative to the cutting surface 114 may be varied by rotating the threaded member 180 to raise or lower the insert member 166 within the cut-out 136. As noted, the member 180 may be a bolt, or it may have, e.g., a knurled knob to facilitate adjustment by hand by the pathologist.

Figure 8:
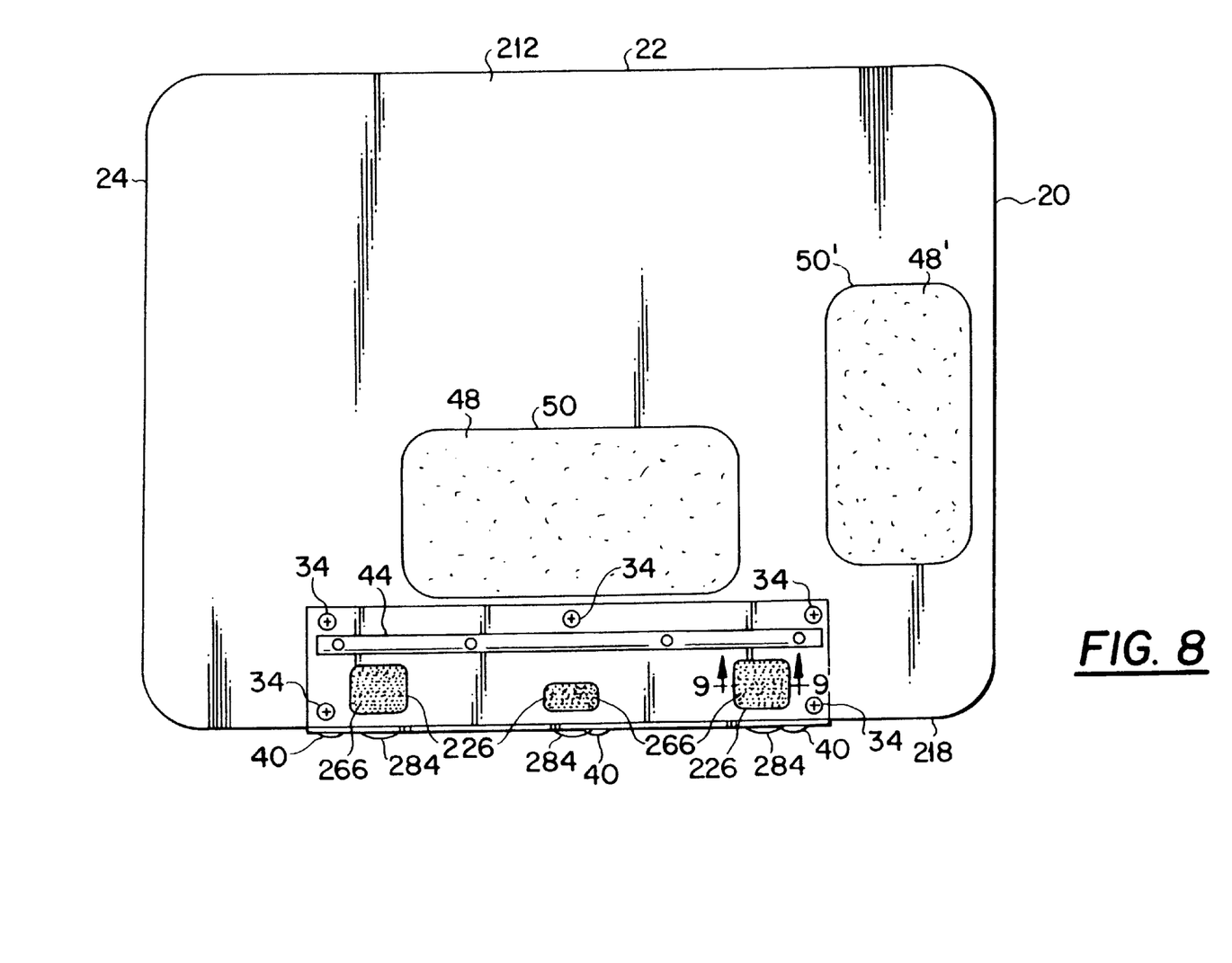
FIG. 8 is a plan view of yet another embodiment of a grossing board according to the invention.
Figure 9:
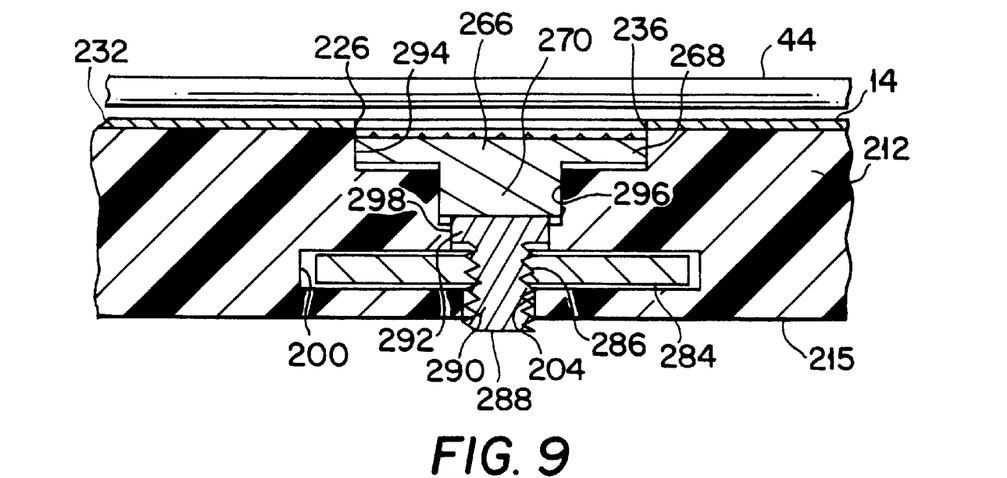
FIG. 9 is a section view board taken along line 9—9 in FIG. 8.
Figure 10:
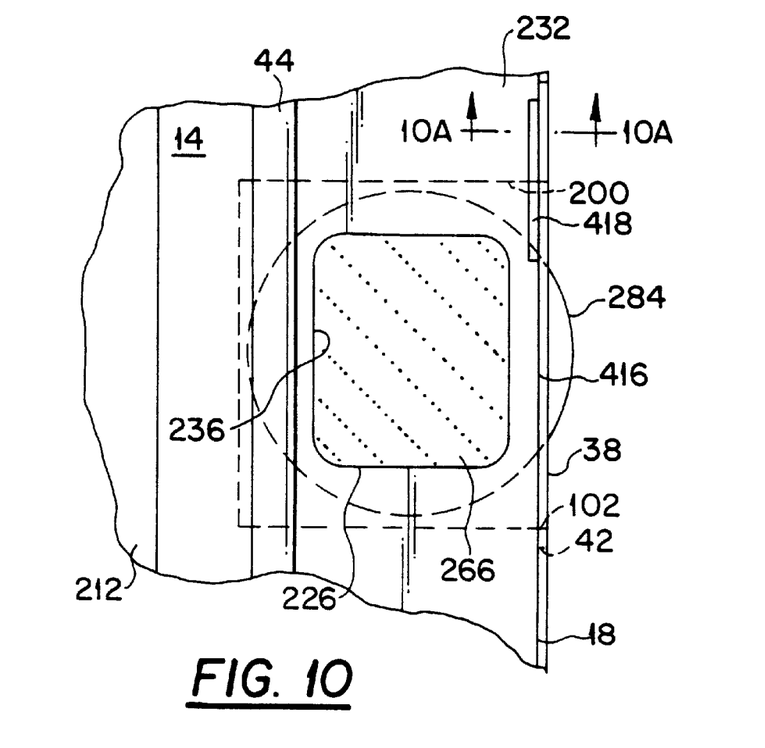
FIG. 10 is a detailed plan view of a tissue-receiving depression shown in FIG. 8.
Figure 11:
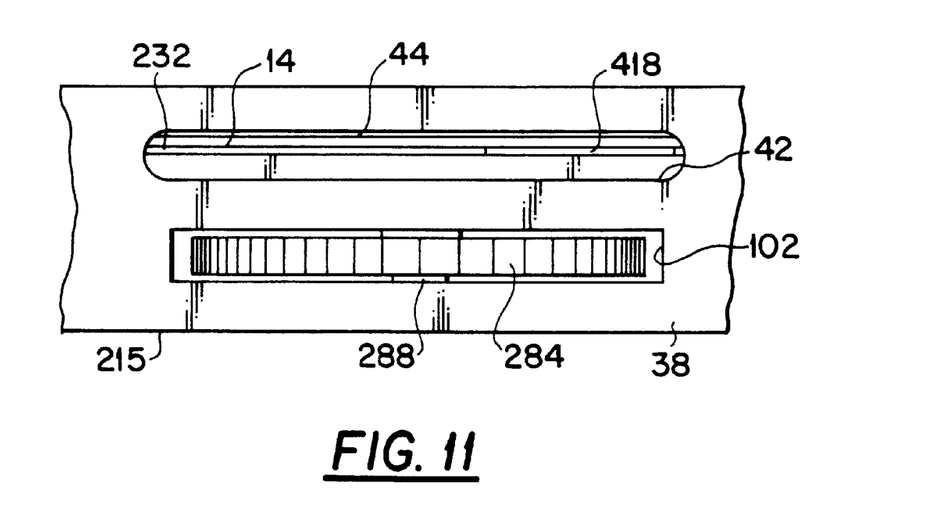
FIG. 11 is a close-up, side view of the tissue-receiving depression portion of the grossing board shown in FIG. 10.

Another similar embodiment of a grossing board is illustrated in FIGS. 8–11, and also allows adjustment of the depth of the depressions 226. In particular, a thumb wheel 284 is used to raise and lower the insert members 266. The thumb wheel 284 fits within pocket 200, which is substantially a rectangular recess formed within the cutting board 212 and open at the side surface 218, and has a threaded central opening 286. A rectangular slot 202 is formed in the first knife-guiding member 238 to allow the thumb wheel 284 to extend through it, as shown in FIGS. 8, 10, and 11. The thumb wheel 284 may preferably be formed with knurling or circumferentially spaced ribs (see, for example, FIG. 11) on an outer periphery thereof to facilitate manual manipulation of the thumb wheel 284.

A threaded member 288 extends through the threaded opening 286. The threaded member 288 includes a threaded, post portion 290 (which makes engagement with the threaded opening 286) and an upper, bearing portion 292 with a non-circular, keyed profile. Like the preceding embodiment, the cut-out 236 has a stepped configuration, with a first recess 294 within which the platform portion 268 of the insert member 266 fits and a circular bore 296, within which the post portion 270 of the insert member 266 fits.

Furthermore, the cut-out 236 includes a non-circular opening 298, the profile of which corresponds to the non-circular profile of the upper portion 292 of the threaded member 288 to receive it in keyed fashion. The noncircular opening 298 and the upper portion 292 of the threaded member 288 cooperate to prevent the threaded member 288 from rotating relative to the cutting board 12. A portion of the threaded member 288 extending downwardly past the thumb wheel 284 is disposed within a bore 204 (of smaller cross section than the pocket 200) which extends between the pocket 200 and the lower surface 215 of the cutting board 212.

As the thumb wheel 284 is rotated, the threaded member 288 is prevented from rotating relative to the cutting board 12 by the keyed relation of the non-circular opening 298 and the upper portion 292 of the threaded member 288. Therefore, as the thumb wheel 284 is rotated relative to the threaded member 288, the threaded member 288 moves vertically and hence raises or lowers the insert member 266. Thus, the depth of the depression 226 can be adjusted by the pathologist simply by rotating the thumb wheel 284.

Figure 10A:
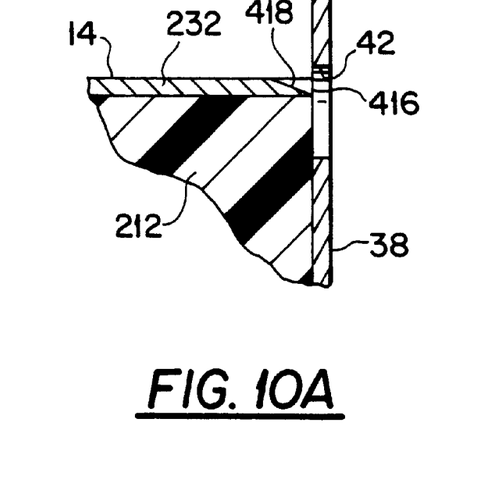
FIG. 10A is a section view taken along line 10A—10A in FIG. 10.

One other feature of the present invention is illustrated in FIGS. 10 and 10A. As shown, an outer edge 416 of the bearing plate 232 preferably has ramped portions 418 formed therein. The ramped portions 418 are positioned within the edge 416, generally adjacent the tissue-receiving depressions 226. The ramped portions 418 may be an incline or fillet formed in the edge 416 to facilitate insertion of the blade through the corresponding slit 42.

Figure 12:
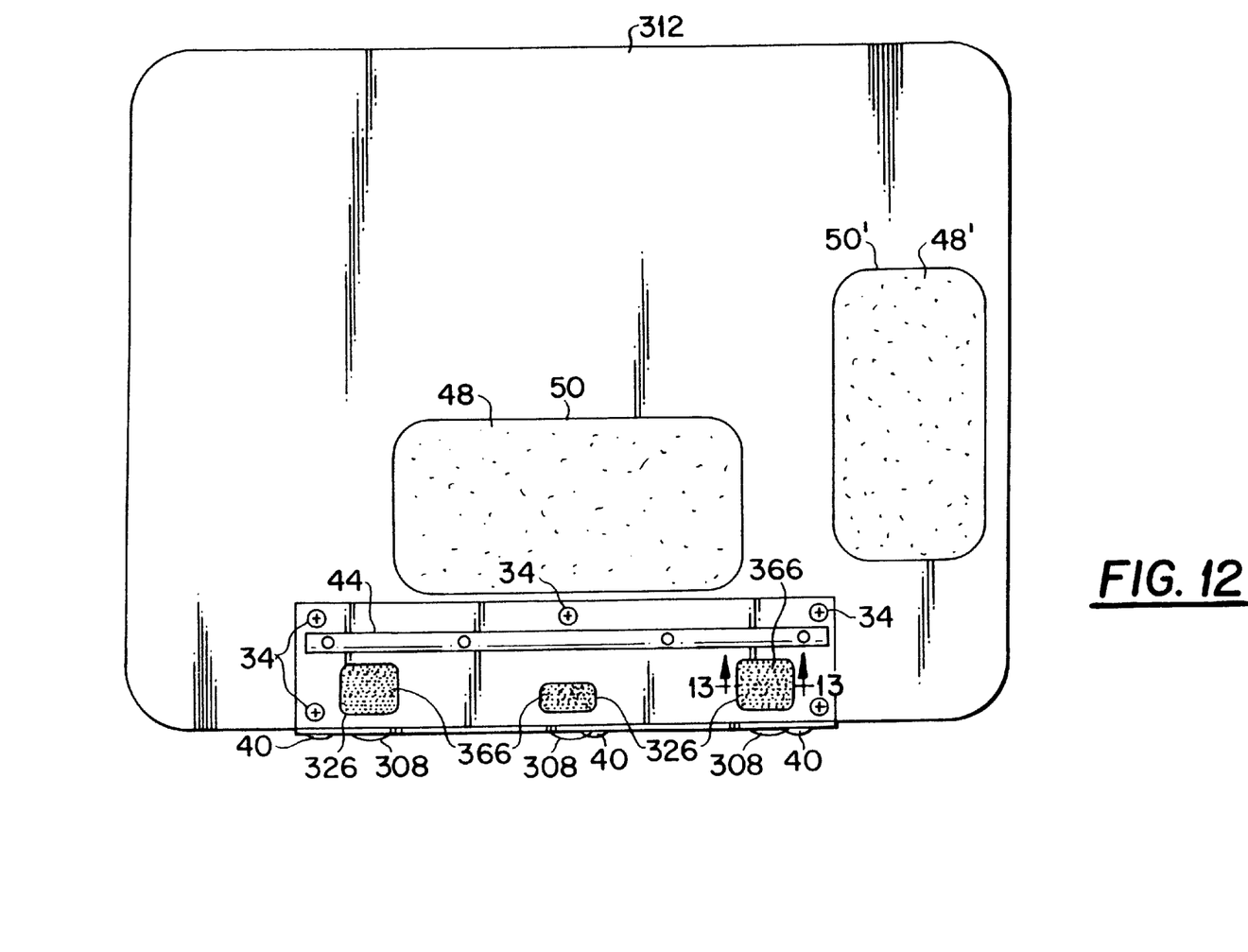
FIG. 12 is a plan view of yet another embodiment of a grossing board according to the invention.
Figure 13:
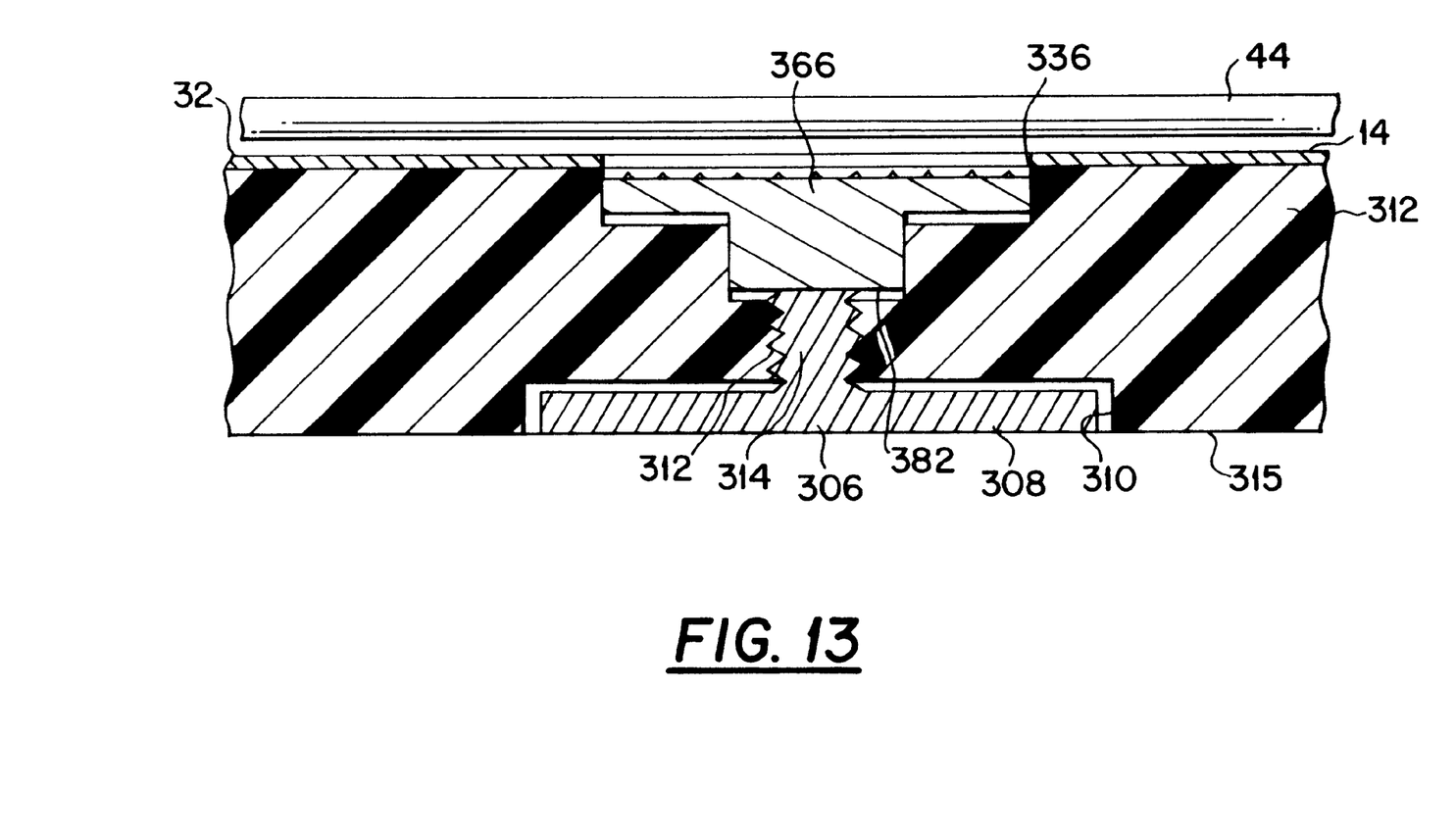
FIG. 13 is a section view taken along the line 13—13 in FIG. 12.

Another contemplated embodiment of a grossing board according to the invention is illustrated in FIGS. 12 and 13. In this embodiment, threaded member 306 includes an integral thumb wheel portion 308. A recess 310 is provided in the lower surface 315 of the cutting board 312, within which recess 310 the thumb wheel portion 308 of the threaded member 306 is disposed. The insert member 366 fits within the cut-out 336. A threaded opening 312 extends between the cut-out 336 and the recess 310. A threaded portion 314 of the threaded member 306 is screwed into and extends through the threaded opening 312. As discussed with reference to the embodiment shown in FIGS. 8, 10, and 11, the thumb wheel portion 308 may be provided with knurling or annularly spaced ribs on an outer periphery thereof to facilitate manual adjustment of the thumb wheel portion 308.

An end of the threaded member 306, opposite the thumb wheel portion 308, abuts and supports the bottom surface 382 of the insert member 366. As the thumb wheel portion 308 is rotated, the insert member 366 is raised or lowered by the threaded member 306.

Other embodiments of the invention will occur to those having skill in the art. These and other embodiments are deemed to be within the scope of the following claims.

We claim:

1. A grossing board for preparing tissue samples, said grossing board comprising:
    a cutting board having an upper, cutting surface;
    a tissue-receiving depression formed in said cutting board and extending downward from the upper, cutting surface of said cutting board, said tissue-receiving depression having a lower, tissue-receiving surface that is essentially parallel to the upper, cutting surface of said cutting board; and
    at least one knife-guiding member attached to said cutting board and configured to receive a tissue-cutting knife and hold the blade generally against the upper, cutting surface of said cutting board so as to facilitate the making of tissue cuts which are essentially parallel to the upper, cutting surface and yield a gross tissue sample having an essentially uniform and reproducible thickness from one sample to another.

2. The grossing board of claim 1, wherein the depth of said tissue-receiving depression is adjustable.

3. The grossing board of claim 2, further comprising a moveable insert member disposed within said tissue-receiving depression, an upper surface of said moveable insert member forming said lower, tissue-receiving surface of said tissue-receiving depression.

4. The grossing board of claim 3, further comprising a threaded member which bears against a lower surface of said moveable insert member, said threaded member causing said moveable insert member to rise within said tissue-receiving depression, to decrease the depth thereof, and said threaded member permitting or causing said moveable insert member to retract or be retracted within said tissue-receiving depression, to increase the depth thereof.

5. The grossing board of claim 4, wherein said threaded member is disposed within said cutting board and is able to rotate relative to said cutting board and wherein rotation of said threaded member relative to said cutting board causes said threaded member to move axially or translationally relative to said cutting board.

6. The grossing board of claim 5, wherein said threaded member is a bolt which is accessible so as to be rotated from a surface of said cutting board that is opposite to the upper, cutting surface of said cutting board.

7. The grossing board of claim 5, wherein said threaded member comprises a threaded post portion and a rigidly connected thumb wheel portion by means of which said threaded post portion is caused to rotate relative to said cutting board.

8. The grossing board of claim 4, wherein said threaded member is rotationally fixed relative to said cutting board, said grossing board further comprising a thumb wheel through which said threaded member passes in threaded engagement therewith, said thumb wheel being free to rotate relative to said cutting board, whereby rotation of said thumb wheel relative to said threaded member causes said threaded member to move axially or translationally relative to said cutting board.

9. The grossing board of claim 8, wherein said first and said second knife-guiding members extend essentially parallel to each other; said first knife-guiding member is configured with at least one slit formed therein which holds the blade portion horizontally; and said second knife-guiding member is configured with a gap formed between the upper, cutting surface and a bottom portion of said second knife-guiding member which is essentially parallel to the upper, cutting surface such that the blade portion is inserted through both of said at least one slit and said gap.

10. The grossing board of claim 1, wherein said at least one knife-guiding member comprises a plate mounted to a working side of said cutting board, said plate extending above the cutting surface of said cutting board and having a knife-receiving slit formed therein and extending generally parallel to said cutting surface, said knife-receiving slit being positioned to form a gap through which a tissue-cutting knife can pass in overlying relation to the cutting surface of said cutting board.

11. The grossing board of claim 1, wherein said at least one knife-guiding member comprises a rail member that is mounted to said cutting board in parallel, spaced relation to the cutting surface of said cutting board, said rail member being spaced from the cutting surface of said cutting board by an amount to define a knife-receiving gap through which a tissue-cutting knife can pass in overlying relation the cutting surface of said cutting board.

12. The grossing board of claim 1, further comprising a bearing plate mounted in a plate-receiving depression formed in said cutting board, said bearing plate having an upwardly facing surface that forms said cutting surface and an aperture formed therein, walls of said aperture surrounding said tissue-receiving depression.

13. The grossing board of claim 1, wherein
   said at least one knife-guiding member comprises a plate mounted to a working side of said cutting board, said plate extending above the cutting surface of said cutting board and having a knife-receiving slit formed therein and extending generally parallel to said cutting surface, said knife-receiving slit being positioned to form a gap through which a tissue-cutting knife can pass in overlying relation to the cutting surface of said cutting board;
   said grossing board further comprises a bearing plate mounted in a plate-receiving depression formed in said cutting board, said bearing plate having an upwardly facing surface that forms said cutting surface and an aperture formed therein, walls of said aperture surrounding said tissue-receiving depression; and
   said bearing plate has a beveled or ramped portion, accessible through said knife-receiving slit, to facilitate insertion of said knife through said knife-receiving slit.

14. The grossing board of claim 1, comprising a plurality of tissue-receiving depressions.

15. The grossing board of claim 14, wherein said plurality of tissue-receiving depressions have different depths.

16. The grossing board of claim 14, wherein said plurality of tissue-receiving depressions have different lengths and/or widths.

17. The grossing board of claim 1, further comprising at least one insert that is formed from a material that is softer than said cutting board, said at least one insert being disposed in a corresponding at least one insert-receiving depression formed in an upper surface of said cutting board.

18. The grossing board of claim 17, wherein said at least one insert is formed from cork.

19. A grossing board for preparing tissue samples, said grossing board comprising:
   a cutting board having an upper, cutting surface;
   at least one tissue-receiving depression formed in said cutting board and which extends downward from the upper, cutting surface of said cutting board, said at least one tissue-receiving depression having a lower, tissue-receiving surface essentially parallel to the upper, cutting surface of said cutting board and providing said at least one tissue-receiving depression with a depth of less than 4 millimeters; and
   first and second knife-guiding members attached to said cutting board and spaced apart from each other, said first and said second knife-guiding members configured to guide a blade portion of a tissue-cutting knife which is drawn in a direction essentially parallel to the lower cutting surface.

20. A method of using the grossing board of claim 19, comprising:
   placing a tissue sample in said at least one tissue-receiving depression,
   inserting said blade portion into said first and said second knife-guiding members, and
   drawing said blade portion through said tissue sample in a direction essentially parallel to the lower cutting surfaces of said gross board and producing a tissue cut of less than 4 millimeters in thickness.

* * * * *